(12) United States Patent
Chiang et al.

(10) Patent No.: US 11,911,377 B2
(45) Date of Patent: Feb. 27, 2024

(54) METHOD FOR TREATING HYPERTENSION BY USING COMPOUND

(71) Applicant: Fu Jen Catholic University, New Taipei (TW)

(72) Inventors: Fu-Tien Chiang, New Taipei (TW); Wei-Chao Chiu, New Taipei (TW)

(73) Assignee: FU JEN CATHOLIC UNIVERSITY, New Taipei (TW)

( * ) Notice: Subject to any disclaimer, the term of this patent is extended or adjusted under 35 U.S.C. 154(b) by 147 days.

(21) Appl. No.: 17/517,796

(22) Filed: Nov. 3, 2021

(65) Prior Publication Data

US 2023/0119423 A1   Apr. 20, 2023

(30) Foreign Application Priority Data

Oct. 20, 2021   (TW) .................. 110138970

(51) Int. Cl.
  *A61K 31/47*   (2006.01)
  *A61P 9/12*   (2006.01)
  *A61K 31/4152*   (2006.01)

(52) U.S. Cl.
  CPC .......... *A61K 31/47* (2013.01); *A61K 31/4152* (2013.01); *A61P 9/12* (2018.01)

(58) Field of Classification Search
  None
  See application file for complete search history.

(56) References Cited

U.S. PATENT DOCUMENTS 9,951,024 B2 *   4/2018   Zheng .................. C07D 231/36

OTHER PUBLICATIONS

Wirth et al., "G12-G13-LARG-mediated signaling in vascular smooth muscle is required for salt-induced hypertension", 2008, Nature Medicine, 14(1), pp. 64-68. (doi:10.1038/nm1666) (Year: 2008).*

Deng et al., "Pyrazolidine-3,5-dione derivatives as potent non-steroidal agonists of farnesoid X receptor: Virtual screening, synthesis, and biological evaluation", 2008, Bioorganic & Medicinal Chemistry Letters, 18(20), pp. 5497-5502. (doi:10.1016/j.bmcl.2008.09.027) (Year: 2008).*
Guilluy et al., "The Rho exchange factor Arhgef1 mediates the effects of angiotensin II on vascular tone and blood pressure", 2010, Nature Medicine, 16(2), pp. 183-190. (doi:10.1038/nm.2079) (Year: 2010).*
Shang et al., "Rational Design of Small Molecule Inhibitors Targeting RhoA Subfamily Rho GTPases", 2012, Chemistry & Biology, 19(6), pp. 699-710. (DOI 10.1016/j.chembiol.2012.05.009) (Year: 2012).*
Shang et al., "Small-molecule inhibitors targeting G-protein-coupled Rho guanine nucleotide exchange factors", 2013, Proceedings of the National Academy of Sciences (PNAS), 110(8), pp. 3155-3160. (www.pnas.org/cgi/doi/10.1073/pnas.1212324110) (Year: 2013).*
National Center for Biotechnology Information. "PubChem Compound Summary for CID 9552914, Rhosin" PubChem, https://pubchem.ncbi.nlm.nih.gov/compound/Rhosin. Accessed Feb. 8, 2023. Created Oct. 23, 2006. (Year: 2006).*
Wei-Chiao Chiu et al., "Small chemical compounds Y16 and Rhosin can inhibit calcium sensitization pathway in vascular smooth muscle cells of spontaneously hypertensive rats", Journal of the Formosan Medical Association 120 (2021) 1863-1868, Apr. 21, 2021, Abstract Only.

* cited by examiner

*Primary Examiner* — Jeffrey S Lundgren
*Assistant Examiner* — Michael J Schmitt
(74) *Attorney, Agent, or Firm* — WPAT, P.C

(57) ABSTRACT

The present disclosure provides a method for treating hypertension by using a compound, wherein the compound is selected from the group consisting of: (E)-4-(3-(3-methyl benzyloxy)benzylidene)-1-phenylpyrazolidine-3,5-dione, (2R)-2-amino-3-(2,3-dihydro-1H-inden-1-yl)-N'-((E)-quinolin-7-ylmethylene)propane hydrazide, and a combination thereof. The present disclosure uses a small molecule compound (E)-4-(3-(3-methyl benzyloxy)benzylidene)-1-phenylpyrazolidine-3,5-dione, (2R)-2-amino-3-(2,3-dihydro-1H-inden-1-yl)-N'-((E)-quinolin-7-ylmethylene)propane hydrazide or a combination thereof, which can be developed as a therapeutic drug for lowering blood pressure, whether it is taken orally or injected.

9 Claims, 11 Drawing Sheets

METHOD FOR TREATING HYPERTENSION BY USING COMPOUND

CROSS-REFERENCE TO RELATED APPLICATION

This application claims priority of Taiwan patent application No. 110138970, filed on Oct. 20, 2021, the content of which is incorporated herein in its entirety by reference.

BACKGROUND OF THE INVENTION

1. Field of the Invention

The present invention relates to a method for treating hypertension by using a compound.

2. The Prior Art

The hypertension is one of the most important diseases in the world. Its prevalence rate accounts for about 25% of the entire population, about 30% for people over 50, and about 50% for people over 65. It ranks ninth among the diseases with high mortality in Taiwan, and is closely related to the second heart disease and the third stroke.

Development of drug treatments for hypertension, from diuretics, sympathetic nerve blockers, calcium channel inhibitors, angiotensin converting enzyme inhibitors to angiotensin II receptor blockers in the past 20 or 30 years. Many drugs have been developed, but there are still about 15-20% of refractory hypertension, which must be treated with more than three drugs, and each hypertension drug has its side effects, especially the angiotensin II receptor, blocking all the signal transductions after the receptor, including the positive (lowering blood pressure) and negative (side effect) effects, and it does not have specificity.

In order to solve the above-mentioned problems, those skilled in the art urgently need to develop novel medicaments for treating hypertension for the benefit of a large group of people in need thereof.

SUMMARY OF THE INVENTION

A primary objective of the present invention is to provide a method for treating hypertension, comprising administering to a subject in need thereof a pharmaceutical composition comprising an effective amount of a compound, wherein the compound is selected from the group consisting of: (E)-4-(3-(3-methyl benzyloxy)benzylidene)-1-phenylpyrazolidine-3,5-dione, (2R)-2-amino-3-(2,3-dihydro-1H-inden-1-yl)-N'-((E)-quinolin-7-ylmethylene)propane hydrazide, and a combination thereof.

According to an embodiment of the present invention, the hypertension is spontaneous hypertension.

According to an embodiment of the present invention, the spontaneous hypertension is treated by inhibiting interaction between leukemia-associated Rho guanine nucleotide exchange factor (LARG) and a RhoA protein in a vascular smooth muscle cell (VSMC).

According to an embodiment of the present invention, the spontaneous hypertension is treated by reducing phosphorylation of myosin phosphatase target subunit 1 (MYPT1) in a vascular smooth muscle cell (VSMC).

According to an embodiment of the present invention, when the (E)-4-(3-(3-methyl benzyloxy)benzylidene)-1-phenylpyrazolidine-3,5-dione is administered alone, the effective amount of the (E)-4-(3-(3-methyl benzyloxy)benzylidene)-1-phenylpyrazolidine-3,5-dione is at least 5 mg/kg.

According to an embodiment of the present invention, when the (2R)-2-amino-3-(2,3-dihydro-1H-inden-1-yl)-N'-((E)-quinolin-7-ylmethylene)propane hydrazide is administered alone, the effective amount of the (2R)-2-amino-3-(2,3-dihydro-1H-inden-1-yl)-N'-((E)-quinolin-7-ylmethylene)propane hydrazide is at least 10 mg/kg.

According to an embodiment of the present invention, when the (E)-4-(3-(3-methyl benzyloxy)benzylidene)-1-phenylpyrazolidine-3,5-dione and the (2R)-2-amino-3-(2,3-dihydro-1H-inden-1-yl)-N'-((E)-quinolin-7-ylmethylene)propane hydrazide are administered in combination, the effective amount of the (E)-4-(3-(3-methyl benzyloxy)benzylidene)-1-phenylpyrazolidine-3,5-dione is at least 3 mg/kg, and the effective amount of the (2R)-2-amino-3-(2,3-dihydro-1H-inden-1-yl)-N'-((E)-quinolin-7-ylmethylene)propane hydrazide is at least 7 mg/kg.

According to an embodiment of the present invention, the pharmaceutical composition further comprises a pharmaceutically acceptable carrier.

According to an embodiment of the present invention, the pharmaceutical composition is in a dosage form for parenteral administration.

According to an embodiment of the present invention, the pharmaceutical composition is in a dosage form for oral administration.

In summary, the compound of the present invention has the effect on inhibiting interaction between leukemia-associated Rho guanine nucleotide exchange factor (LARG) and a RhoA protein in vascular smooth muscle cells (VSMCs) by in vitro cell experiments, reducing phosphorylation of myosin phosphatase target subunit 1 (MYPT1) in VSMCs, and effectively reducing the blood pressure of spontaneously hypertensive rats by in vivo animal experiments, thereby achieving the effect of treating hypertension. Therefore, the small molecule compounds of (E)-4-(3-(3-methyl benzyloxy)benzylidene)-1-phenylpyrazolidine-3,5-dione, (2R)-2-amino-3-(2,3-dihydro-1H-inden-1-yl)-N'-((E)-quinolin-7-ylmethylene)propane hydrazide or a combination thereof are used in the present invention, and developed as a therapeutic drug for lowering blood pressure. It is effective whether it is administered orally or injected. By injection, blood pressure can be lowered quickly, and within different doses, blood pressure can be lowered by 20-40% within one hour. Compared with traditional antihypertensive drugs (i.e., angiotensin II receptors), its superiority is even greater.

If it is made into an oral dosage form, it can be adjusted to an appropriate antihypertensive effect according to different doses and dynamic changes of the drug. (E)-4-(3-(3-methyl benzyloxy)benzylidene)-1-phenylpyrazolidine-3,5-dione and (2R)-2-amino-3-(2,3-dihydro-1H-inden-1-yl)-N'-((E)-quinolin-7-ylmethylene)propane hydrazide achieve the effect of lowering blood pressure by inhibiting Rho guanine nucleotide exchange factor (Rho GEF)/LARG small G protein, the downstream of the signaling transduction pathway of angiotensin II receptor, thereby blocking the activation of Rho A/Rho kinase and myosin light chain phosphatase (MLCP). Its role is specific. The compound of the present invention are different from angiotensin type II receptors, which block all the signal transductions after the receptors, including positive (lowering blood pressure) and negative (side effect) effects without specificity. In addition, from the observation of animal experiments, high-dose (E)-4-(3-(3-methyl benzyloxy)benzylidene)-1-phenylpyrazolidine-3,5-dione or (2R)-2-amino-3-(2,3-dihydro-1H-inden-1-yl)-N'-

((E)-quinolin-7-ylmethylene)propane hydrazide does not cause changes in animal blood (blood cells), organs (e.g., heart, lung, liver, and kidney) and tissues. Therefore, (E)-4-(3-(3-methyl benzyloxy)benzylidene)-1-phenylpyrazolidine-3,5-dione, (2R)-2-amino-3-(2,3-dihydro-1H-inden-1-yl)-N'-((E)-quinolin-7-ylmethylene)propane hydrazide or the combination thereof has the potential to become a safe hypertension drug.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

FIG. 6B, Y16; FIG. 6C, Rhosin and FIG. 6D, Y16+Rhosin); their ECG, HR, and BP were recorded; the figures here show the data of representative samples; abbreviations: BPM, beats per minute.

FIGS. 7A and 7B show that Y16 decreases BP and HR in a dose-dependent manner but has no significant effect on HR, in which FIG. 7A shows that Y16 had no effects on BP at 0.2 mg/kg and 1 mg/kg; at 5 mg/kg, Y16 decreased BP of 21% and last only for 30 minutes (see FIG. 7A, 5 mg/kg group, 79%±13%, versus 0 min; p=0.0081); at 10 mg/kg, Y16 could also decrease BP of 21% and lasting for over 60 minutes (see FIG. 7A, 10 mg/kg group, 79%±12%, versus 0 min; p=0.0007); when the dose increased 20 mg/kg, it achieved the maximum blood pressure reduction effect of 42% in 20 minutes and last for more than 60 minutes (see FIG. 7A, 20 mg/kg group, 58%±8%, versus 0 min; p=0.0187); FIG. 7B shows that Y16 slightly decreased HR; when the dose increased to 20 mg/kg, Y16 could reduce the HR by 16% for 30 minutes (see FIG. 7B, 20 mg/kg group, 84%±8%, versus 0 min; p=0.1067), but the difference was not statistically significant; the data from each rat was compared before and after drug administration; results are expressed as the means of at least four independent experiments plus or minus standard deviation; *p<0.05, #p<0.01, $ p<0.005, &p<0.001 versus the group before drug administration (0 minute); abbreviations: BPM, beats per minute.

FIGS. 8A and 8B show that Rhosin can decrease BP in a dose-dependent manner but slightly influence the HR, in which FIG. 8A shows the effects of Rhosin on BP; it was not statistically significant at 5 mg/kg of Rhosin; when the dosage increased to 10 mg/kg, the maximum decrease of BP by 28% occurred in 60 minutes, and lasted for up to 90 minutes (see FIG. 8A, 10 mg/kg group, 72%±6%, versus 0 min; p<0.0001); at 20 mg/kg, a large of BP reduction was observed at 30 minutes 34% lasting up to 90 min (FIG. 8A, 20 mg/kg group, 66%±1%, versus 0 min; p=0.0002), while the maximum reduction was 41% at 60 min (see FIG. 8A, 20 mg/kg group, 59%±2%, versus 0 min; p=0.0016); FIG. 8B shows a high Rhosin dose (20 mg/kg) decreased HR of 21% by 60 minutes (see FIG. 8B, 20 mg/kg group, 79%±4%, versus 0 min; p=0.0188); meanwhile, a medium dose (10 mg/kg) had also lowered their HR by 10% at 60 minutes (see FIG. 8B, 10 mg/kg, 90%±7%, versus 0 min; p=0.0058); the data from each rat was compared before and after drug administration; results are expressed as the means of at least four independent experiments plus or minus standard deviation; *p<0.05, #p<0.01, $ p<0.005, &p<0.001 versus the group before drug administration (0 minute).

DETAILED DESCRIPTION OF THE PREFERRED EMBODIMENT

Figure 1:
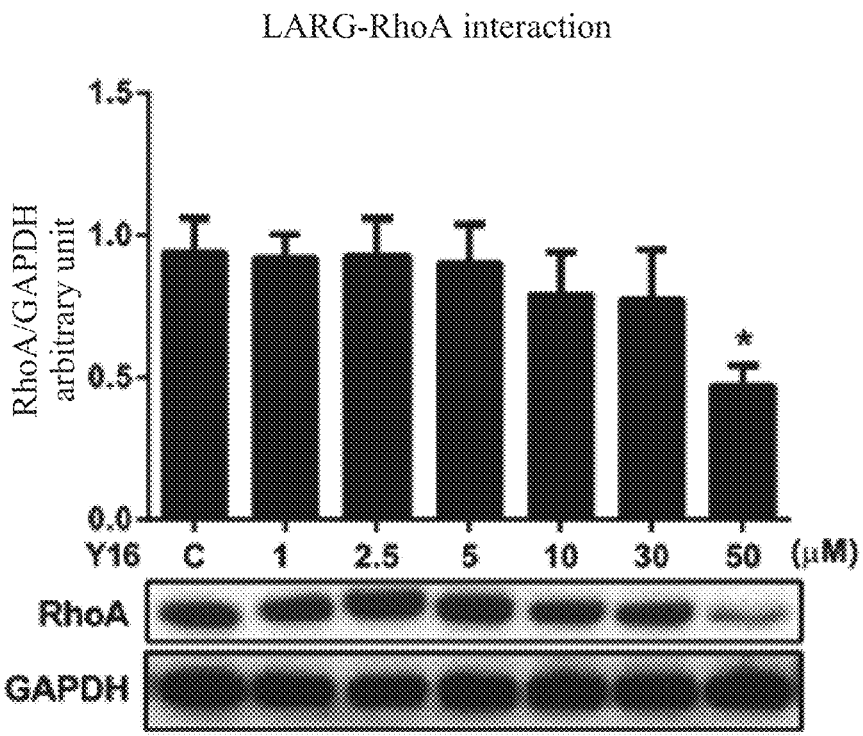
FIG. 1 shows cellular effects of (E)-4-(3-(3-methyl benzyloxy)benzylidene)-1-phenylpyrazolidine-3,5-dione (hereinafter referred to as Y16) inhibition of leukemia-associated Rho guanine nucleotide exchange factor (LARG) binding to RhoA, in which primary cultured vascular smooth muscle cells (VSMCs) from spontaneously hypertensive rats (SHRs) were treated with Y16 at the indicated concentrations for 24 h in serum-free M199 media; the cells were subsequently stimulated with $10^{-7}$M angiotensin II (Ang II) for 10 min and were then subjected to the co-immunoprecipitation method, and the LARG-RhoA interaction was examined; Western blot analysis was used to measure protein levels, with glyceraldehyde-3-phosphate dehydrogenase (GAPDH) as the internal control; relative amounts of the GTP-bound form of the RhoA were quantified by densitometry measurements and normalized to GAPDH; data were expressed as the mean±standard deviation of five independent experiments; the group not treated with Y16 is the control group (i.e., the symbol C in the figure); * indicates that compared with the control group, $p<0.05$.

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

According to the present invention, the data were expressed as mean±standard deviation with n representing the number of independent experiments. Variance testing and the unpaired Student's t-test were employed to analyze the results. A P-value of less than 0.05 was considered significant. All statistical analyses were performed using SPSS19.0.

According to the present invention, the statistical analysis used in the following examples is described as follows. For the physiological signals recording, the data from different time intervals of each rat was compared with that from before Y16 and Rhosin administration. Considering the differences of physiological conditions among individuals, the BP and HR are not calculated by the absolute value measured, but by the percentage of the BP or HR measured at each time point relative to those measured before administration (0 minutes). All data were representative of at least four independent experiments.

According to the present invention, Rhosin, CAS 1173671-63-0, is a cell-permeable compound that directly targets Rho GEF binding domain, thereby prevents Rho from interacting with its GEFs. The chemical name is (2R)-2-amino-3-(2,3-dihydro-1H-inden-1-yl)-N'-((E)-quinolin-7-ylmethylene)propane hydrazide. Rhosin has a molecular weight of 358.4, the chemical formula of $C_{20}H_{18}N_6O$, and the following structural formula:

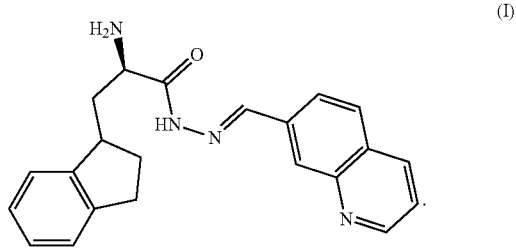 [SMILES: N[C@H](CC1CCc2ccccc21)C(=O)N/N=C/c1ccc2cccnc2c1]

(I)

According to the present invention, Y16, CAS 429653-73-6, is a Rho inhibitor II, and also a leukemia-associated Rho guanine nucleotide exchange factor (LARG) Rho binding domain blocker. The chemical name is (E)-4-(3-(3-methyl benzyloxy)benzylidene)-1-phenylpyrazolidine-3,5-dione. Y16 has a molecular weight of 384.43, the chemical formula of $C_{24}H_{20}N_2O_3$, and the following structural formula:

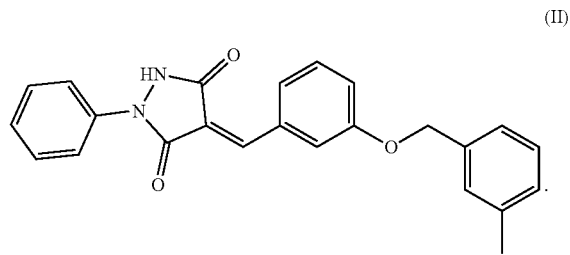 [SMILES: Cc1cccc(COc2cccc(/C=C3\C(=O)NN(c4ccccc4)C3=O)c2)c1]

(II)

As used herein, the term "effective concentration" refers to the amount of medicaments needed to directly treat individuals suffering from hypertension. The effective concentration may be different depending on the biological species or individual differences to be treated, but the effective concentration can be determined experimentally by, for example, concentration escalation.

As used herein, the term "treating" or "treatment" refers to alleviating, reducing, ameliorating, relieving or controlling one or more clinical signs of a disease or disorder, and lowering, stopping, or reversing the progression of severity regarding the condition or symptom being treated.

According to the present invention, the pharmaceutical composition can be manufactured to a dosage form suitable for parenteral or oral administration, using techniques well known to those skilled in the art, including, but not limited to, injection (e.g., sterile aqueous solution or dispersion), sterile powder, tablet, troche, lozenge, pill, capsule, dispersible powder or granule, solution, suspension, emulsion, syrup, elixir, slurry, and the like.

The pharmaceutical composition according to the present invention may be administered by a parenteral route selected from the group consisting of: intraperitoneal injection, subcutaneous injection, intramuscular injection and intravenous injection.

According to the present invention, the pharmaceutical composition may further comprise a pharmaceutically acceptable carrier which is widely used in pharmaceutically manufacturing techniques. For example, the pharmaceutically acceptable carrier can comprise one or more reagents selected from the group consisting of solvent, emulsifier, suspending agent, decomposer, binding agent, excipient, stabilizing agent, chelating agent, diluent, gelling agent, preservative, lubricant, absorption delaying agent, liposome, and the like. The selection and quantity of these reagents fall within the scope of the professional literacy and routine techniques of those skilled in the art.

According to the present invention, the pharmaceutically acceptable carrier comprises a solvent selected from the group consisting of water, normal saline, phosphate buffered saline (PBS), sugar-containing solution, aqueous solution containing alcohol, and combinations thereof.

Example 1

Evaluation of Effect Regarding Y16 on Inhibiting Leukemia-Associated Rho Guanine Nucleotide Exchange Factor (LARG)-RhoA Interaction in Spontaneously Hypertensive Rat (SHR) Vascular Smooth Muscle Cells (VSMCs)

The culture procedure of the primary cultured vascular smooth muscle cells (VSMCs) used in this example or the following examples is as follows. SHRs were anesthetized with Zoletil 50, and the thoracic aortas were immediately excised. The samples were then carefully cleaned of connective tissue and adherent fat. Each isolated aorta was cut open longitudinally, followed by endothelial removal by gently grazing the intimal surface. The denuded aortas were cut into approximately 2 mm² sections and then placed with the intimal side down. The M199 medium supplemented with 20% fetal bovine serum and antibiotics (100 U/ml penicillin and 100 μg/ml streptomycin) were then gently added to cover the tissues without disturbing the orientation of the explants. VSMCs were allowed to grow out from the explants for 7-10 days culture, and the tissues were removed. Cultured VSMCs which exhibited>95% positive immunostaining for smooth muscle α-actin were used in the experiments.

The treatment method of the small molecule compounds used in this example or the following examples is as follows. Small molecule compounds were dissolved in pure water to test their effects on the VSMCs. Different concentrations of Y16 or the combination of Y16+Rhosin were administered for 24 hours, followed by stimulation with $10^{-7}M$ angiotensin II (Ang II) for 10 min. The Y16 concentrations used were as follows: 1 μM, 2.5 μM, 5 μM, 10 μM, 30 μM, 50 μM.

The procedure of cell harvest and protein extraction used in this example or the following examples is as follows. Culture dishes were placed on ice and washed twice with ice-cold phosphate-buffered saline (PBS). All subsequent procedures were performed over ice. Lysis buffer (cold PBS solution, pH 7.4, containing 1 mmol/L ethylenediamine tetraacetic acid (EDTA), 25 mmol/L HEPES, 150 mmol/L NaCl, 10 mmol/L $MgCl_2$, 10% glycerol, and 1% igepal® CA-630 (a non-ionic liquid surfactant)) was added to the plates, followed by 2 min incubation on ice. Cells were then scraped off and transferred to Eppendorf tubes. The samples were sonicated for 5 s and then centrifuged at 12000×g for 15 min at 4° C. The supernatant was transferred to a new tube and kept on ice. The protein concentrations were determined using a BSA Protein Assay kit.

The procedure of co-immunoprecipitation used in this example or the following examples is as follows. Protein A/G agarose beads were washed twice with phosphate buffer solution, and a 50% protein A/G agarose bead working solution was prepared with phosphate buffer salt solution. 100 µl of the working solution was added to a 1 ml sample and shaken for 10 min (in an EP tube on ice placed on a horizontal shaker) at 4° C. to remove non-specific binding proteins. The sample was then centrifugation at 12000×g for 15 min at 4° C. and the supernatant was then transferred to a new centrifuge tube to remove the protein A/G agarose beads. Anti-LARG antibody (1:100) was added to 500 µg of total protein, and the mixture was shaken slowly at 4° C. overnight. Next, 100 µl of protein A agarose beads were added to capture the antigen-antibody complex, and the antigen-antibody mixture was slowly shaken overnight at 4° C. Centrifugation at 12000×g was then applied for 5 s, and the precipitate was collected and washed 3 times with precooled phosphate buffer solution. The agarose bead-antigen-antibody complex was then suspended with sample buffer, mixed gently, and centrifuged, and the supernatant could also be temporarily frozen at −20° C. for later electrophoresis.

The procedure of Western blot analysis used in this example or the following examples is as follows. Equal amounts of protein (40 µg) were separated by electrophoresis on a 12% or 6% polyacrylamide gel and transferred onto polyvinylidene difluoride membranes. Non-specific binding sites were blocked using Protein-Free Blocking Buffer (Pierce Chemical, Rockford, Illinois, USA) for 1 h at 24° C. The membranes were then incubated overnight at 4° C. with anti-RhoA (1:1000) (Santa Cruz Biotechnology Inc, CA, USA), anti-phospho-MYPT1 (Thr 696) (1:2000) (Millipore Corporation, Billerica, MA, USA), anti-total-MYPT1 (1:2000)(Molecular Devices, Sunnyvale, CA, USA), or anti-GAPDH (1:1000) (Chemicon, Temecula, CA, USA). Following exposure to a horseradish peroxidase-conjugated secondary anti-mouse or anti-rabbit antibody, the membranes were subjected to ECL reagent (Millipore Corporation, Billerica, USA). Signals were visualized using a UVP Imaging System (UVP) or with X-ray film, and the results were expressed as the densitometric ratio of target protein/GAPDH or phosphor-MYPT1/total-MYPT1.

To examine whether Y16 is effective in suppressing LARG-RhoA interaction and RhoA activity in VSMCs, VSMCs grown in serum-free media were treated with different concentrations of Y16 for 24 hours, followed by stimulation with $10^{-7}$M Ang II for 10 min. The result is shown in FIG. 1.

FIG. 1 shows cellular effects of Y16 inhibition of LARG binding to RhoA, in which primary cultured VSMCs from SHRs were treated with Y16 at the indicated concentrations for 24 h in serum-free M199 media; the cells were subsequently stimulated with $10^{-7}$M Ang II for 10 min and were then subjected to the co-immunoprecipitation method, and the LARG-RhoA interaction was examined; Western blot analysis was used to measure protein levels, with GAPDH as the internal control; relative amounts of the GTP-bound form of the RhoA were quantified by densitometry measurements and normalized to GAPDH; data were expressed as the mean±standard deviation of five independent experiments; the group not treated with Y16 is the control group (i.e., the symbol C in the figure); * indicates that compared with the control group, p<0.05.

As shown in FIG. 1, Y16 dose-dependently inhibited the LARG-RhoA complex formation induced by Ang II. At the concentration of 50 µM of Y16, the inhibitory effect reached a statistically significant difference (0.939±0.121 for the control group versus 0.469±0.074 of 50 µM for the Y16 group, normalized to GAPDH, p value<0.001).

Example 2

Evaluation of Effect Regarding Y16 on Reducing Phosphorylation of Myosin Phosphatase Target Subunit 1 (MYPT1) in SHR VSMCs Y16 can reduce the formation of the phospho-MYPT1 on myosin light chain phosphatase (MLCP) stimulated by Ang II, which occurs downstream of RhoA. The experimental procedure of this example is the same as that described in Example 1. The result is shown in FIG. 2.

Figure 2:
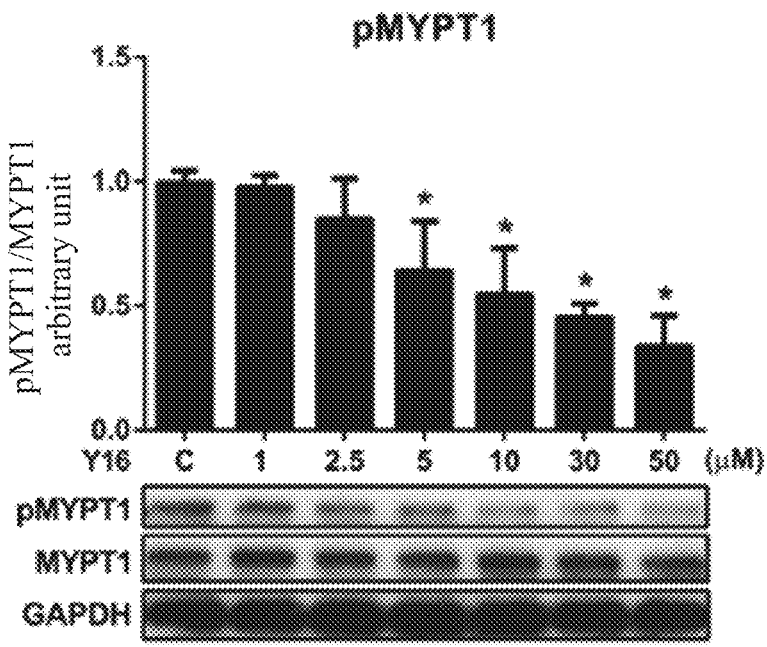
FIG. 2 shows levels of myosin phosphatase target subunit 1 (MYPT1) phosphorylation after Y16 administered to primary cultured VSMCs from SHRs, in which rat primary VSMCs were treated with Y16 at the indicated concentrations for 24 h in serum-free media; cells were subsequently stimulated with $10^{-7}$M Ang II for 10 min, and the levels of MYPT1 phosphorylation were examined; Western blot analysis was used to measure protein levels, with total MYPT1 protein and glyceraldehyde-3-phosphate dehydrogenase (GAPDH) as the internal control; relative amounts of phospho-MYPT1 (pMYPT1) were quantified by densitometry measurements and normalized to total-MYPT1; data were expressed as the mean±standard deviation of five independent experiments; the group not treated with Y16 is the control group (i.e., the symbol C in the figure); * indicates that compared with the control group, $p<0.05$.

FIG. 2 shows levels of MYPT1 phosphorylation after Y16 administered to primary cultured VSMCs from SHRs, in which rat primary VSMCs were treated with Y16 at the indicated concentrations for 24 h in serum-free media; cells were subsequently stimulated with $10^{-7}$M Ang II for 10 min, and the levels of MYPT1 phosphorylation were examined; Western blot analysis was used to measure protein levels, with total MYPT1 protein and GAPDH as the internal control; relative amounts of phospho-MYPT1 (pMYPT1) were quantified by densitometry measurements and normalized to total-MYPT1; data were expressed as the mean±standard deviation of five independent experiments; the group not treated with Y16 is the control group (i.e., the symbol C in the figure); * indicates that compared with the control group, p<0.05.

The result in FIG. 2 shows a dose-dependent inhibition of MYPT1 phosphorylation by Y16. In particular, at the concentration of 5 µM of Y16, the inhibitory effect reached a statistically significant difference (0.994±0.048 versus 0.642±0.199, normalized to total-MYPT1, P=0.041, as shown in FIG. 2).

Example 3

Evaluation of Effect Regarding Rhosin on Enhancing the Inhibitory Effect of Y16 on LARG Binding to RhoA in SHR VSMCs In this example, the inhibitory effects were tested when Y16 and Rhosin were used together. The experimental procedure of this example is the same as that described in Example 1. The result is shown in FIG. 3.

Figure 3:
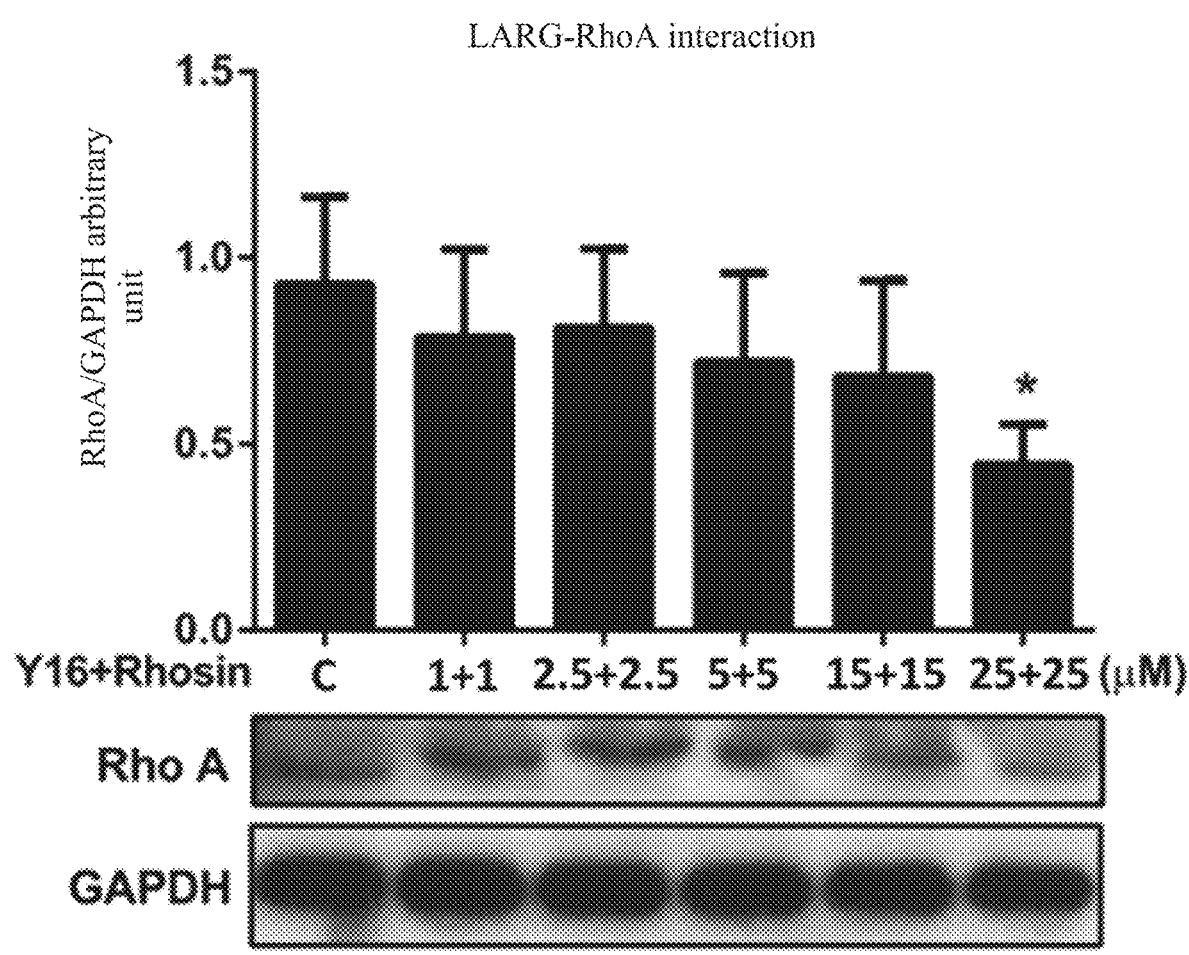
FIG. 3 shows cellular effects of Y16 in combination with (2R)-2-amino-3-(2,3-dihydro-1H-inden-1-yl)-N'-((E)-quinolin-7-ylmethylene)propane hydrazide (hereinafter referred to as Rhosin) to inhibit LARG binding to RhoA in primary cultured VSMCs from SHRs, in which primary VSMCs from SHRs were treated with Y16 in combination with Rhosin at the indicated concentrations for 24 h in serum-free media; cells were subsequently stimulated with $10^{-7}$M Ang II for 10 min and were then subjected to the co-immunoprecipitation method, and the LARG-RhoA interaction was examined; Western blot analysis was used to measure protein levels, with glyceraldehyde-3-phosphate dehydrogenase (GAPDH) as the internal control; relative amounts of the GTP-bound form of the RhoA were quantified by densitometry measurements and normalized to GAPDH; data were expressed as the mean±standard deviation of five independent experiments; the group not treated with Y16 in combination with Rhosin is the control group (i.e., the symbol C in the figure); * indicates that compared with the control group, $p<0.05$.

FIG. 3 shows cellular effects of Y16 in combination with Rhosin to inhibit LARG binding to RhoA in primary cultured VSMCs from SHRs, in which primary VSMCs from SHRs were treated with Y16 in combination with Rhosin at the indicated concentrations for 24 h in serum-free media; cells were subsequently stimulated with $10^{-7}$M Ang II for 10 min and were then subjected to the co-immunoprecipitation method, and the LARG-RhoA interaction was examined; Western blot analysis was used to measure protein levels, with GAPDH as the internal control; relative amounts of the GTP-bound form of the RhoA were quantified by densitometry measurements and normalized to GAPDH; data were expressed as the mean±standard deviation of five independent experiments; the group not treated with Y16 in combination with Rhosin is the control group (i.e., the symbol C in the figure); * indicates that compared with the control group, p<0.05.

After being combined Rhosin, the inhibitory effect of Y16 on LARG-RhoA interaction reached a statistically significant difference when the concentrations of Y16 and Rhosin were 25 µM, respectively (0.929±0.235 versus 0.446±0.108, normalized to GAPDH, P=0.003, as shown in FIG. 3).

Example 4

Evaluation of Effect Regarding Y16 on Acting Synergistically with Rhosin in Inhibiting MYPT1 Phosphorylation in SHR VSMCs Evaluation of effect regarding Y16 on acting synergistically with Rhosin in inhibiting MYPT1 phosphorylation in SHR VSMCs is explored in this example. The experimental procedure of this example is the same as that described in Example 1. The result is shown in FIG. 4.

Figure 4:
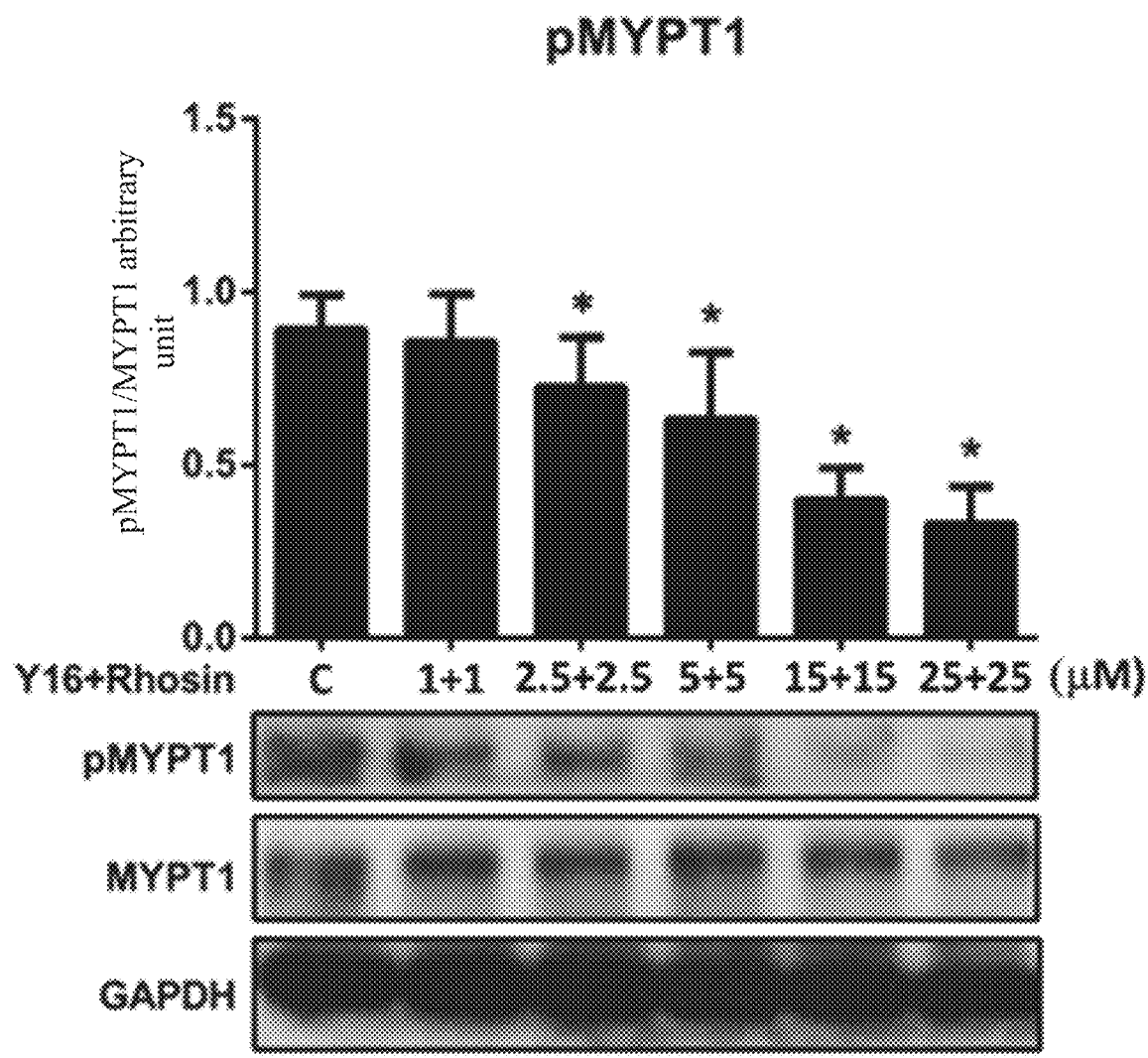
FIG. 4 shows levels of MYPT1 phosphorylation after combined administration of Y16 and Rhosin to primary cultured VSMCs from SHRs, in which primary VSMCs from SHRs were treated with Y16 in combination with Rhosin at the indicated concentrations for 24 h in serum-free media; cells were subsequently stimulated with $10^{-7}$M Ang II for 10 min, and the levels of MYPT1 phosphorylation were examined; Western blot analysis was used to measure protein levels, with total MYPT1 protein and glyceraldehyde-3-phosphate dehydrogenase (GAPDH) as the internal control; relative amounts of phospho-MYPT1 (pMYPT1) were quantified by densitometry measurements and normalized to total-MYPT1; data were expressed as the mean±standard deviation of five independent experiments; the group not treated with Y16 in combination with Rhosin is the control group (i.e., the symbol C in the figure); * indicates that compared with the control group, $p<0.05$.

FIG. 4 shows levels of MYPT1 phosphorylation after combined administration of Y16 and Rhosin to primary cultured VSMCs from SHRs, in which primary VSMCs from SHRs were treated with Y16 in combination with Rhosin at the indicated concentrations for 24 h in serum-free media; cells were subsequently stimulated with $10^{-7}$M Ang II for 10 min, and the levels of MYPT1 phosphorylation were examined; Western blot analysis was used to measure protein levels, with total MYPT1 protein and GAPDH as the internal control; relative amounts of phospho-MYPT1 (pMYPT1) were quantified by densitometry measurements and normalized to total-MYPT1; data were expressed as the mean±standard deviation of five independent experiments; the group not treated with Y16 in combination with Rhosin is the control group (i.e., the symbol C in the figure); * indicates that compared with the control group, $p<0.05$.

When Y16 and Rhosin were combined together, the working concentrations required for the effective inhibition of MYPT1 phosphorylation were significantly decreased (2.5 µM compared with 5 µM for Y16 alone) (0.892±0.099 versus 0.718±0.133, normalized to total-MYPT1, P=0.046, as shown in FIG. 4).

Example 5

Effects of Y16 on Cell Viability of SHR Primary VSMCs

The procedure of 3-(4,5-dimethylthiazol-2-yl)-2,5-diphenyltetrazolium bromide (MTT) assay for cell viability used in this example is as follows. The cytotoxicity results for Y16 or Rhosin were determined using an MTT-based in vitro assay. Briefly, the media from the cell cultures was discarded and carefully aspirated. Next, 50 µL of serum-free media and 50 µL of MTT solution were added into each well. The plate was then incubated at 37° C. for 3 hours. After incubation, 150 µL of MTT solvent (4 mM HCl, 0.1% NP40 in isopropanol) was added into each well. The plate was then wrapped in foil and shaken on an orbital shaker for 15 minutes, and the absorbance was read at OD=590 nm. The result is shown in FIG. 5A and FIG. 5B.

Figure 5A:
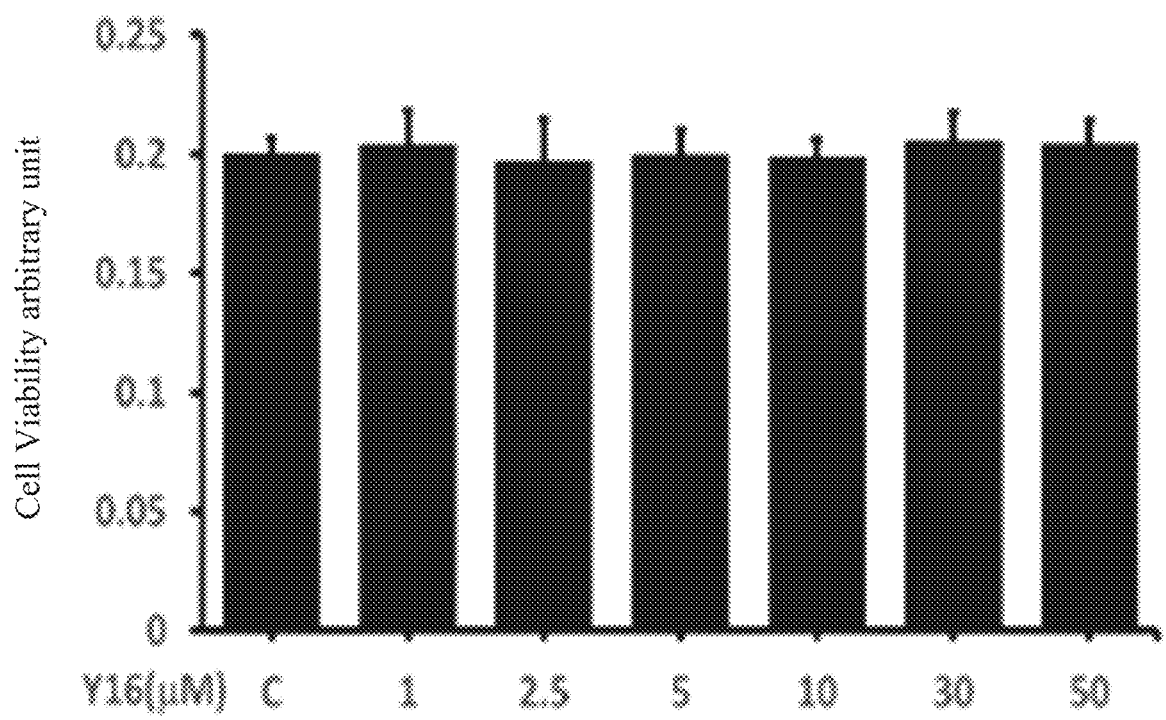
FIGS. 5A and 5B show effects of Y16, or the combination of Y16 and Rhosin, on cell viability of SHR primary VSMCs, in which the effects of Y16 or Y16 in combination with Rhosin on the viability of SHR primary cultured VSMCs were examined; cells were treated with 1, 2.5, 5, 10, 30, or 50 mol/L of Y16 (FIG. 5A) or with 1+1, 2.5+2.5, 5+5, 15+15, or 25+25 mol/L of Y16 in combination with Rhosin (FIG. 5B) for 24 hours in serum-free M199 media; cells were subsequently stimulated with $10^{-7}$M Ang II for 10 min and subjected to a cell cytotoxicity assay; neither Y16 nor Rhosin treatment had any conspicuous effect on the growth of the SHR VSMCs; data were expressed as the mean±standard deviation of five independent experiments; the group not treated with Y16 or Y16 in combination with Rhosin is the control group (i.e., the symbol C in the figure); * indicates that compared with the control group, $p<0.05$.
Figure 5B:
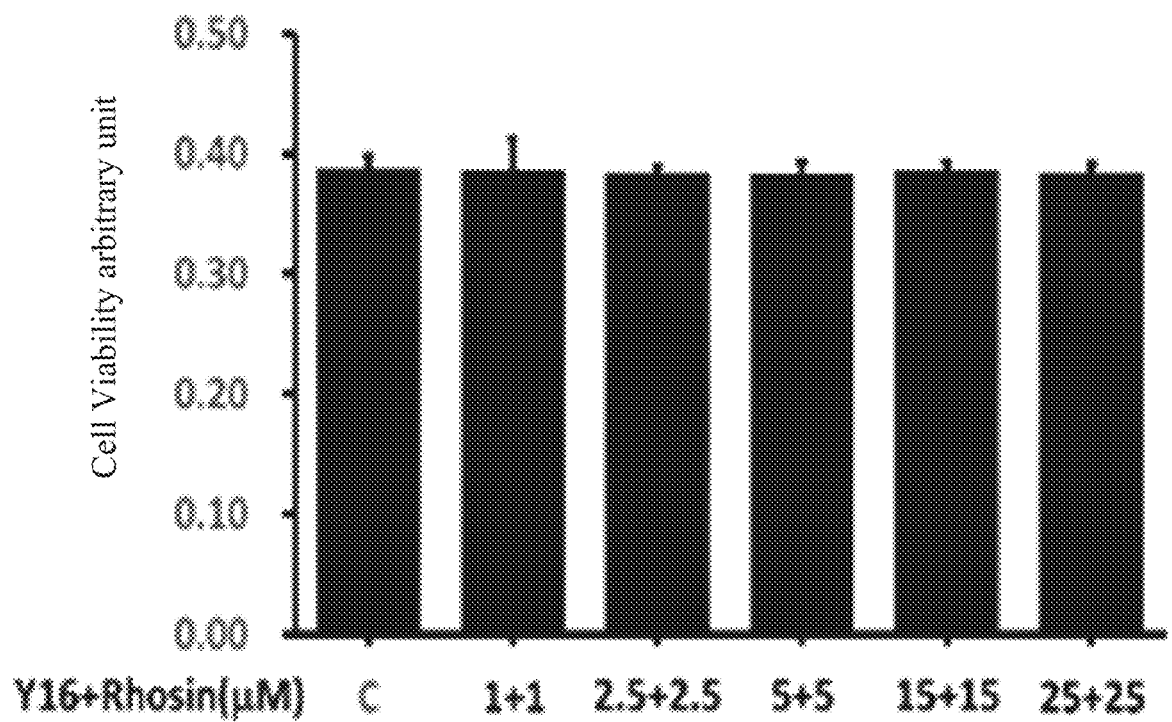
Figure 6A:
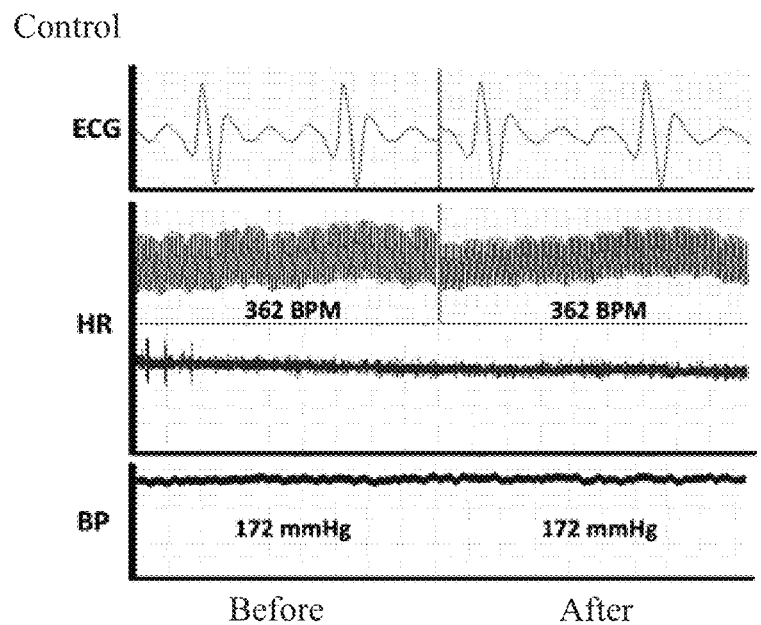
FIGS. 6A to 6D show the data of representative samples including electrocardiography (ECG), heart rate (HR) (beat per minute, BPM), and blood pressure (BP) before and after the administration of Y16 and Rhosin, in which each rat was anesthetized, attached to a physiological signal recording device, and administered different concentrations (doses) of the drugs (FIG. 6A, control.
Figure 6B:
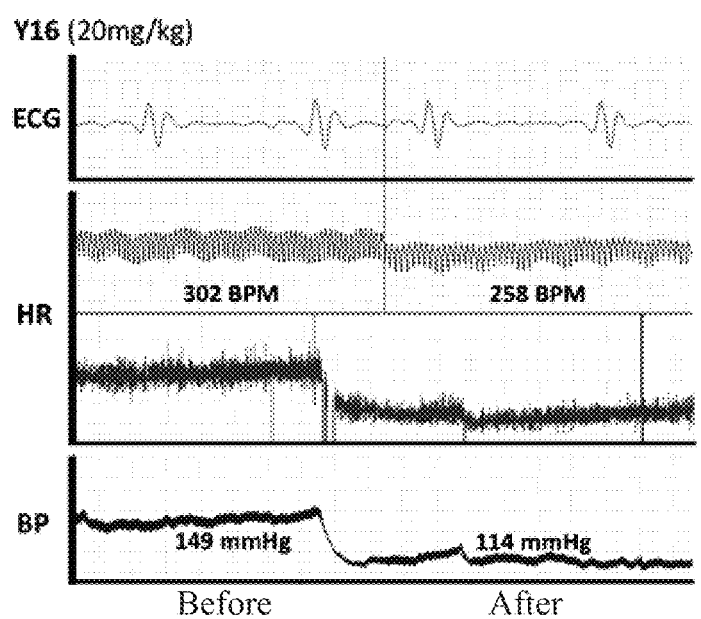
Figure 6C:
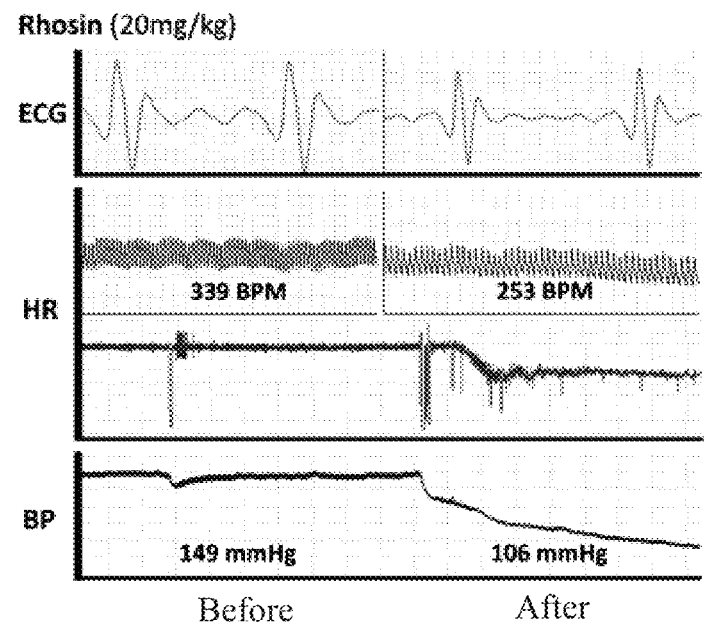
Figure 6D:
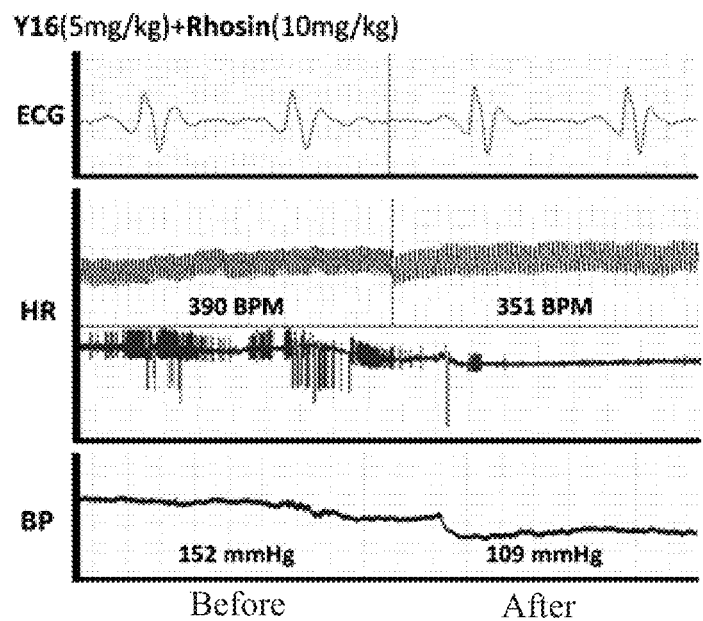

FIGS. 5A and 5B show effects of Y16, or the combination of Y16 and Rhosin, on cell viability of SHR primary VSMCs, in which the effects of Y16 or Y16 combined with Rhosin on the viability of SHR primary cultured VSMCs were examined; cells were treated with 1, 2.5, 5, 10, 30, or 50 µmol/L of Y16 (FIG. 5A) or with 1+1, 2.5+2.5, 5+5, 15+15, or 25+25 µmol/L of Y16 in combination with Rhosin (FIG. 5B) for 24 hours in serum-free M199 media; cells were subsequently stimulated with $10^{-7}$M Ang II for 10 min and subjected to a cell cytotoxicity assay; neither Y16 nor Rhosin treatment had any conspicuous effect on the growth of the SHR VSMCs; data were expressed as the mean±standard deviation of five independent experiments; the group not treated with Y16 or Y16 in combination with Rhosin is the control group (i.e., the symbol C in the figure); * indicates that compared with the control group, $p<0.05$.

The result of this example shows that the reduction of LARG-RhoA interaction or the diminishing p-MYPT1 by Y16 had no conspicuous effect on the growth of the SHR VSMCs. The results showed that the cells were alive, so the decrease in the amount of RhoA or p-MYPT1 on western blot analysis was due to the inhibitory effect of Y16 rather than cell death caused by the toxicity of Y16.

Example 6

Evaluation of Effect Regarding Y16 and Rhosin on Decreasing Blood Pressure (BP) and Heart Rate (HR) in SHRs The animal model used in this example or the following examples is illustrated as follows. The Institutional Animal Care and Use Committee of the Fu Jen Catholic University, New Taipei, Taiwan (Approval No A10660), approved all of the animal procedures and experimental protocols. Male 16-week-old SHRs (body weight range: 350-370 g) were purchased from the National Laboratory Animal Center, Taipei, Taiwan. The animals were housed at a temperature of 21° C. under a 12 h light/dark cycle and fed a regular pellet diet. The animals were divided into three main groups—the Y16 group, the Rhosin group, and the Y16+Rhosin group. Each group was further divided into several subgroups according to the administered Y16 and Rhosin dose. Their concentrations are listed below: Y16 group: 0.2 mg/kg, 1 mg/kg, 5 mg/kg, 10 mg/kg, 20 mg/kg; Rhosin group: 5 mg/kg, 10 mg/kg, 20 mg/kg; Y16+Rhosin group: (Y16, 3 mg+Rhosin, 7 mg)/kg, (Y16, 5 mg+Rhosin, 10 mg)/kg.

The procedure of physiological signals recording and blood tests used in this example or the following examples is as follows. The rats were anesthetized with Zoletil 50 (30 mg/kg, intraperitoneal injection) and then attached to a physiological signal recording device. The Y16 and Rhosin were administered to them by intravenous injection. Their electrocardiography (ECG), heart rate (HR), and blood pressure (BP) measurements were taken for 90 minutes. After observing and recording the physiological signals, blood was drawn from the rats in an appropriate test tube and stored for subsequent tests for complete blood cell count, liver function and renal function. The rats were then sacrificed. Their heart, lungs, liver, and kidneys were removed and stored in paraformaldehyde for further histological examinations. The result is shown in FIGS. 6A to 6D.

FIGS. 6A to 6D show the data of representative samples including electrocardiography (ECG), heart rate (HR) (beat per minute, BPM), and blood pressure (BP) before and after the administration of Y16 and Rhosin, in which each rat was anesthetized, attached to a physiological signal recording device, and administered different concentrations (doses) of the drugs (FIG. 6A, control; 6B, Y16; 6C, Rhosin and 6D, Y16+Rhosin); their ECG, HR, and BP were recorded; the figures here show the data of representative samples; abbreviations: BPM, beats per minute.

Example 7

Evaluation of Effect Regarding Y16 on Decreasing BP and HR in a Dose-Dependent Manner The animal model and experimental procedure of this example are the same as those described in Example 6. The result is shown in FIGS. 7A and 7B.

Figure 7A:
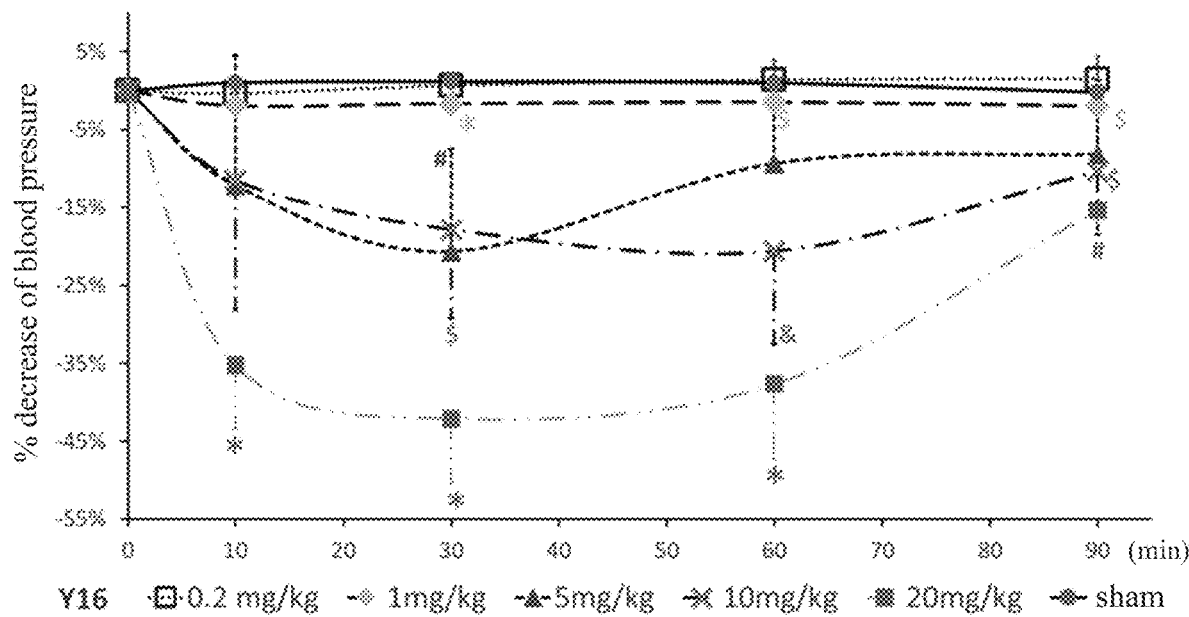
Figure 7B:
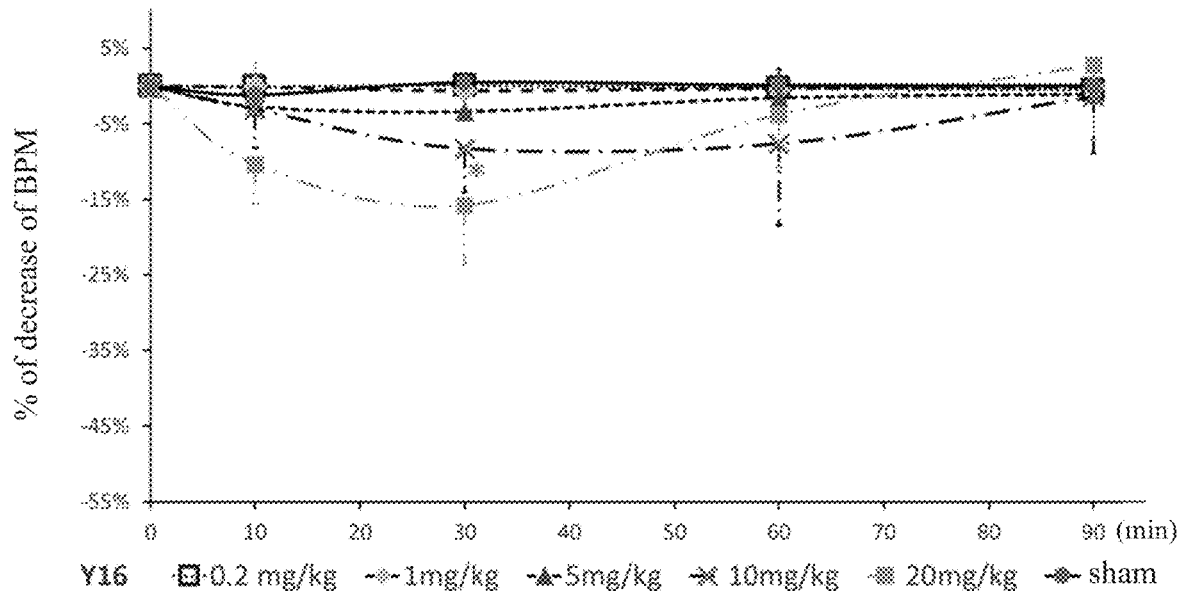

FIGS. 7A and 7B show that Y16 decreases BP and HR in a dose-dependent manner but has no significant effect on HR, in which FIG. 7A shows that Y16 had no effects on BP at 0.2 mg/kg and 1 mg/kg; at 5 mg/kg, Y16 decreased BP of 21% and last only for 30 minutes (see FIG. 7A, 5 mg/kg group, 79%±13%, versus 0 min; p=0.0081); at 10 mg/kg, Y16 could also decrease BP of 21% and lasting for over 60 minutes (see FIG. 7A, 10 mg/kg group, 79%±12%, versus 0 min; p=0.0007); when the dose increased 20 mg/kg, it achieved the maximum blood pressure reduction effect of 42% in 20 minutes and last for more than 60 minutes (see FIG. 7A, 20 mg/kg group, 58%±8%, versus 0 min; p=0.0187); FIG. 7B shows that Y16 slightly decreased HR; when the dose increased to 20 mg/kg, Y16 could reduce the HR by 16% for 30 minutes (see FIG. 7B, 20 mg/kg group, 84%±8%, versus 0 min; p=0.1067), but the difference was not statistically significant; the data from each rat was compared before and after drug administration; results are expressed as the means of at least four independent experiments plus or minus standard deviation; *p<0.05, #p<0.01, $ p<0.005, &p<0.001 versus the group before drug administration (0 minute); abbreviations: BPM, beats per minute. After reaching the maximum effect, the BP gradually returned to the original level after 90 minutes of observation.

Example 8

Evaluation of Effect Regarding Rhosin on Decreasing BP and HR in a Similar Dose-Dependent Manner The animal model and experimental procedure of this example are the same as those described in Example 6. The result is shown in FIGS. 8A and 8B.

Figure 8A:
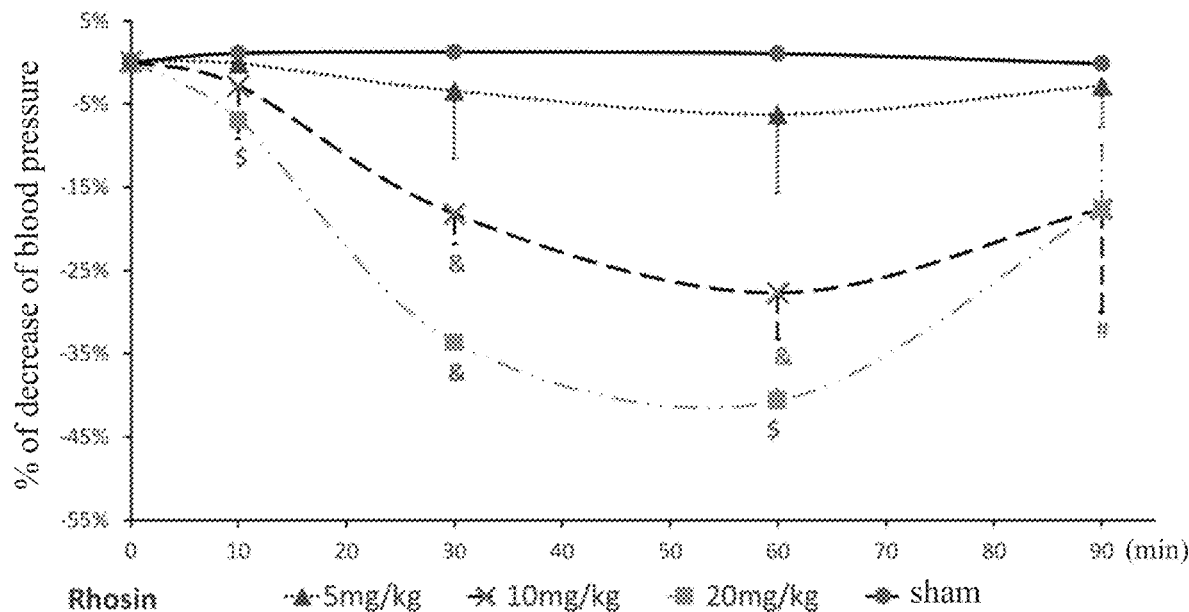
Figure 8B:
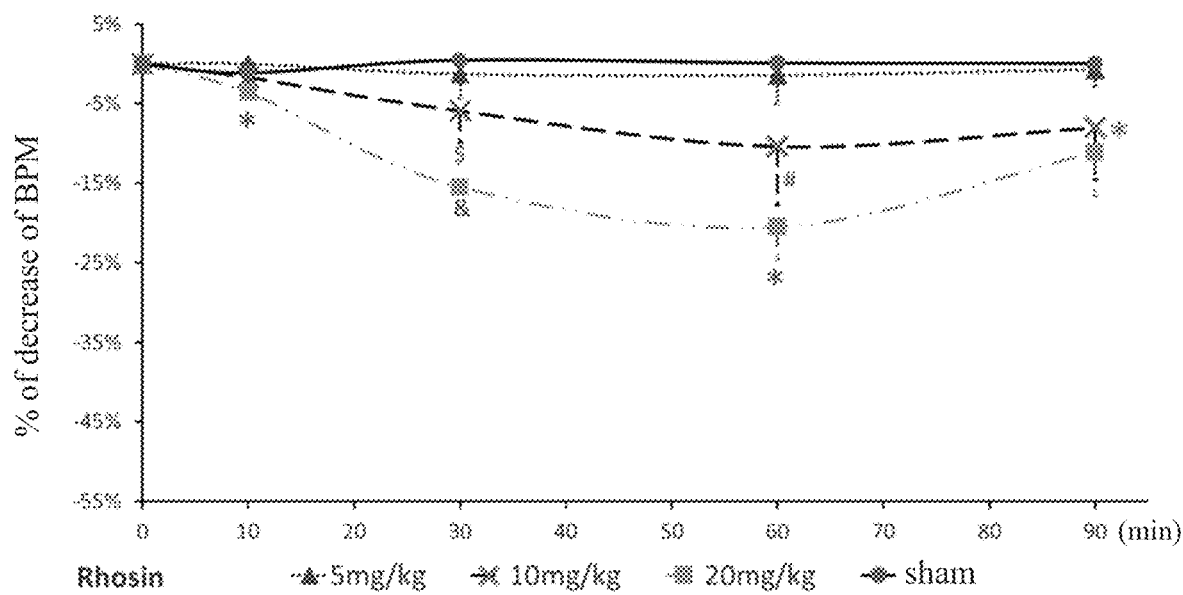

FIGS. 8A and 8B show that Rhosin can decrease BP in a dose-dependent manner but slightly influence the HR, in which FIG. 8A shows the effects of Rhosin on BP; it was not statistically significant at 5 mg/kg of Rhosin; when the dosage increased to 10 mg/kg, the maximum decrease of BP by 28% occurred in 60 minutes, and lasted for up to 90 minutes (see FIG. 8A, 10 mg/kg group, 72%±6%, versus 0 min; p<0.0001); at 20 mg/kg, a large of BP reduction was observed at 30 minutes 34% lasting up to 90 min (FIG. 8A, 20 mg/kg group, 66%±1%, versus 0 min; p=0.0002), while the maximum reduction was 41% at 60 min (see FIG. 8A, 20 mg/kg group, 59%±2%, versus 0 min; p=0.0016); FIG. 8B shows a high Rhosin dose (20 mg/kg) decreased HR of 21% by 60 minutes (see FIG. 8B, 20 mg/kg group, 79%±4%, versus 0 min; p=0.0188); meanwhile, a medium dose (10 mg/kg) had also lowered their HR by 10% at 60 minutes (see FIG. 8B, 10 mg/kg, 90%±7%, versus 0 min; p=0.0058); the data from each rat was compared before and after drug administration; results are expressed as the means of at least four independent experiments plus or minus standard deviation; *p<0.05, #p<0.01, $ p<0.005, &p<0.001 versus the group before drug administration (0 minute). Each dose reached the maximum effect in about 60 minutes, and then at the observed time point, 90 minutes, the BP gradually returned to baseline (FIG. 8A).

Example 9

Evaluation of Effect Regarding Y16 on Acting Additively with Rhosin in Reducing BP Given that single doses of Y16 or Rhosin at high doses would lower BP and HR, a combination of Y16 and Rhosin dose was tested in this example, along with low doses that do not have overt effects on HR. The animal model and experimental procedure of this example are the same as those described in Example 6. The result is shown in FIGS. 9A and 9B.

Figure 9A:
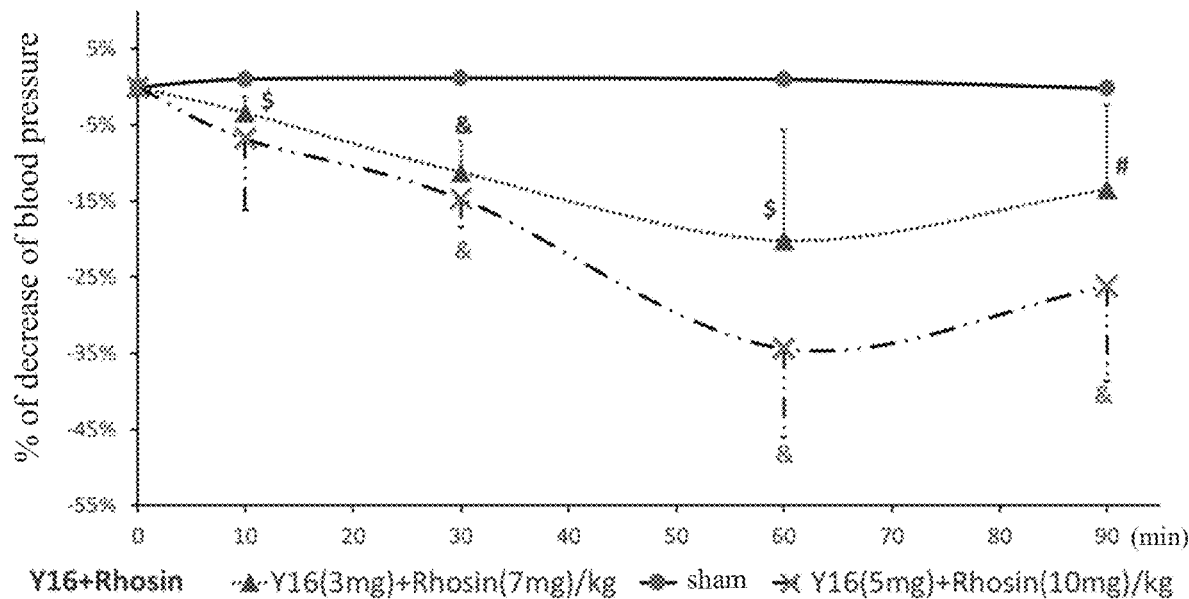
FIG. 9A shows that Y16 and Rhosin synergistically reduced BP in SHRs, where the combination group of Y16 (3 mg/kg)+Rhosin (7 mg/kg) reduced BP by 11% at 30 minutes (89%±4%, versus 0 min; p<0.0001); the maximum BP reduction of 20% (80%±15%, versus 0 min; p=0.0032) occurred at 60 minutes, while a 13% BP reduction was observed at 90 minutes (87%±11%, versus 0 min; p=0.0071); in the Y16 (5 mg/kg)+Rhosin (10 mg/kg) combination, there was a 15% reduction of BP at 30 minutes (85%±4%, versus 0 min; p<0.0001); the maximum BP reduction was 34% (66%±12%, versus 0 min; p<0.0001) occurred at 60 minutes, while a 26% BP reduction was observed at 90 minutes (74%±12%, versus 0 min; p=0.0004); the data from each rat was compared before and after drug administration; results from at least four independent experiments are expressed as the means plus or minus standard deviation; *p<0.05, #p<0.01, $ p<0.005, &p<0.001 versus the group before drug administration (0 minute).
Figure 9B:
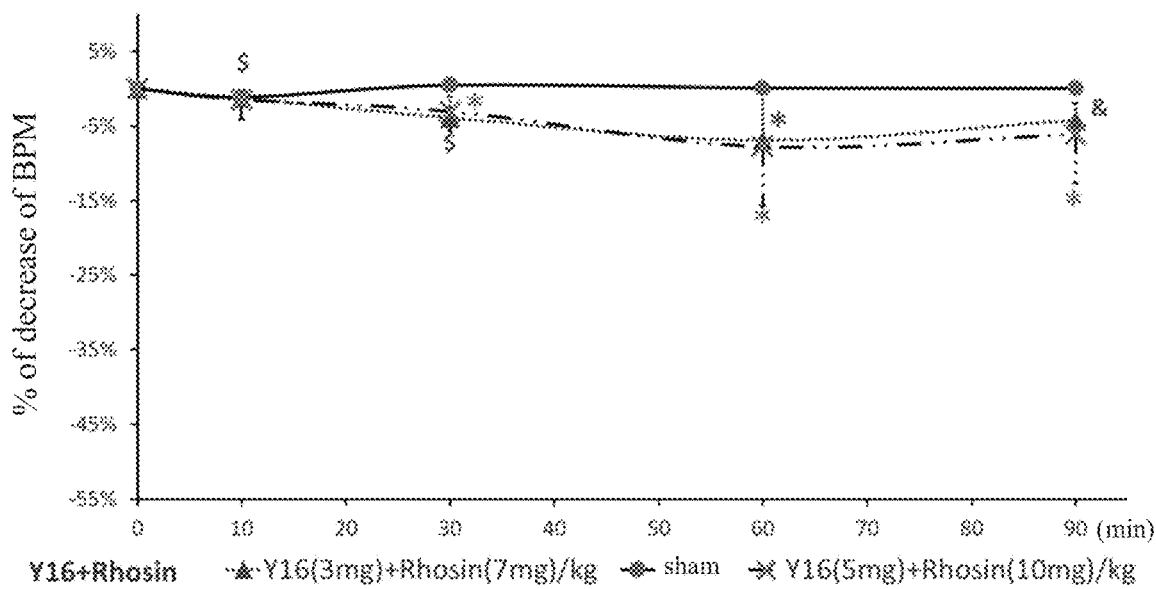
FIG. 9B shows that low dose of Y16 in combination with Rhosin does not excessively lower HR; the Y16 (3 mg/kg)+Rhosin (7 mg/kg) combination maximally lowered the rats' HR by 7% at 60 minutes (93%±6%, versus 0 min; p=0.0148); while the Y16 (5 mg/kg)+Rhosin (10 mg/kg) combination lowered the HR at a maximum of 8% at 60 minutes (92%±8%, versus 0 min; p=0.0396); the data from each rat was compared before and after drug administration; results from at least four independent experiments are expressed as the means plus or minus standard deviation; *p<0.05, #p<0.01, $ p<0.005, &p<0.001 versus the group before drug administration (0 minute).

FIGS. 9A and 9B show that Y16 and Rhosin synergistically reduced BP in SHRs, where the combination group of Y16 (3 mg/kg)+Rhosin (7 mg/kg) reduced BP by 11% at 30 minutes (89%±4%, versus 0 min; p<0.0001); the maximum BP reduction of 20% (80%±15%, versus 0 min; p=0.0032) occurred at 60 minutes, while a 13% BP reduction was observed at 90 minutes (87%±11%, versus 0 min; p=0.0071); in the Y16 (5 mg/kg)+Rhosin (10 mg/kg) combination, there was a 15% reduction of BP at 30 minutes (85%±4%, versus 0 min; p<0.0001); the maximum BP reduction was 34% (66%±12%, versus 0 min; p<0.0001) occurred at 60 minutes, while a 26% BP reduction was observed at 90 minutes (74%±12%, versus 0 min; p=0.0004); FIG. 9B shows that low dose of Y16 in combination with Rhosin does not excessively lower HR; the Y16 (3 mg/kg)+Rhosin (7 mg/kg) combination maximally lowered the rats' HR by 7% at 60 minutes (93%±6%, versus 0 min; p=0.0148); while the Y16 (5 mg/kg)+Rhosin (10 mg/kg) combination lowered the HR at a maximum of 8% at 60 minutes (92%±8%, versus 0 min; p=0.0396); the data from each rat was compared before and after drug administration; results from at least four independent experiments are expressed as the means plus or minus standard deviation; *p<0.05, #p<0.01, $ p<0.005, &p<0.001 versus the group before drug administration (0 minute).

Example 10

Evaluation of Adverse Effects of Y16 and/or Rhosin to Experimental Animals by Blood Tests The animal model and experimental procedure of this example are the same as those described in Example 6. To observe whether the use of Y16 or Rhosin might have adverse effects or even harm to the animals, the blood of rats was drawn for the blood test after collecting the required physiological signals. The result is shown in FIG. 10.

Figure 10:
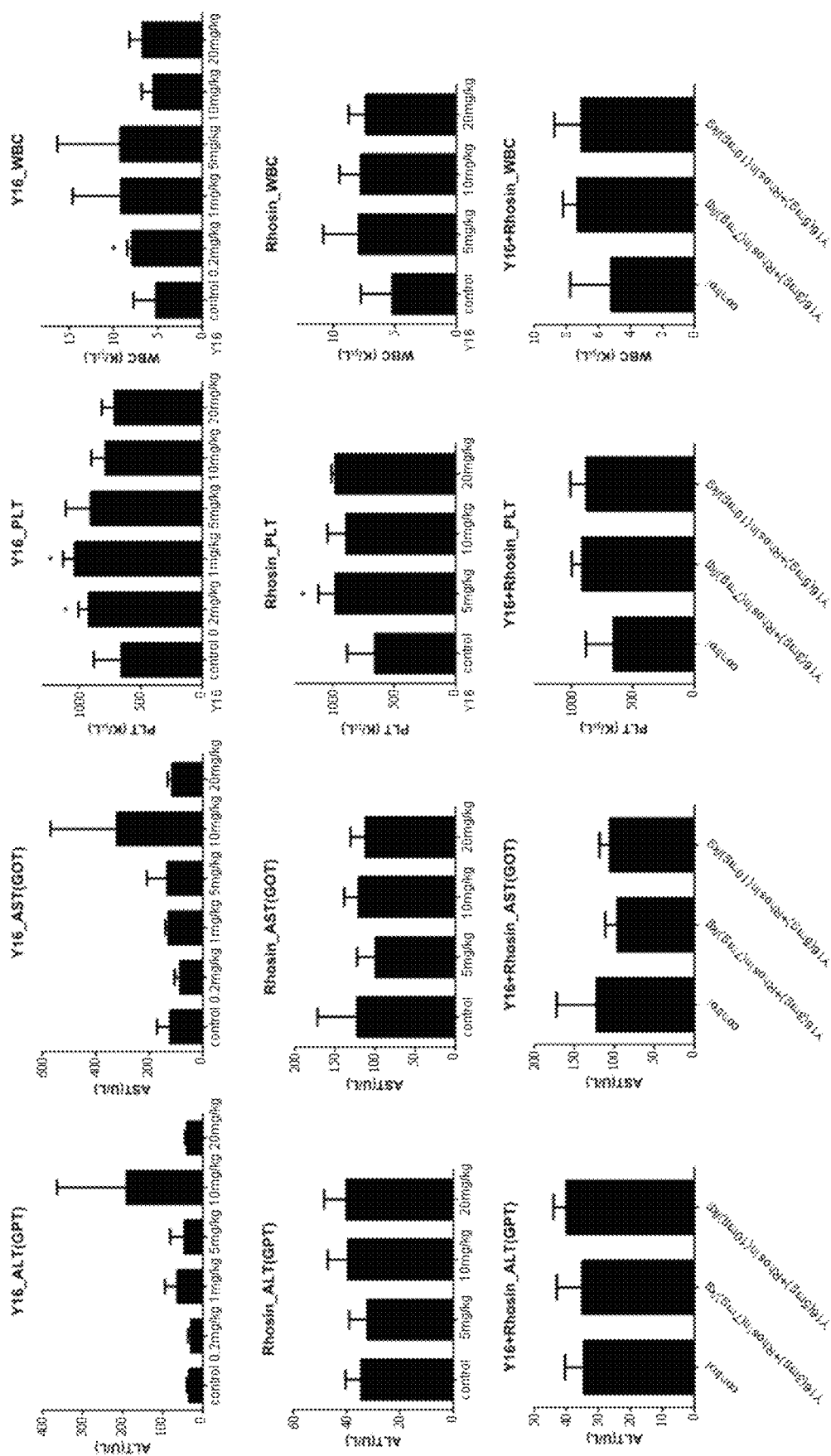
FIG. 10 shows that the Y16 and Rhosin doses used in the experiments did not cause any overt abnormalities to the rats; regarding complete blood cell count and liver function; results are expressed as the means of at least four independent experiments plus or minus standard deviation; *p<0.05 versus the control group; at 0.2 mg/kg, 1 mg/kg of Y16 and 5 mg/kg of Rhosin, the platelets count (PLC) or white blood cell counts (WBC) was slightly high and reach a significant difference; ALT represents alanine transaminase; GPT represents glutamate pyruvate transaminase; PLT represents platelet level; WBC represents white blood cell counts; AST represents aspartate aminotransferase; GOT represents glutamic oxaloacetic transaminase.

FIG. 10 shows that the Y16 and Rhosin doses used in the experiments did not cause any overt abnormalities to the rats; regarding complete blood cell count and liver function; results are expressed as the means of at least four independent experiments plus or minus standard deviation; *p<0.05 versus the control group; at 0.2 mg/kg, 1 mg/kg of Y16 and 5 mg/kg of Rhosin, the platelets count (PLC) or white blood cell counts (WBC) was slightly high and reach a significant difference. Platelet level (PLT) and white blood cell count (WBC) were slightly increased at low drug concentration such as 0.2 mg/kg or 1 mg/kg, which was not related to the administration of Y16 or Rhosin, but might be related to the physiological reaction of operation to animals (anesthesia, intubation, surgery, etc.).

Example 11

Histological Changes of Y16 and/or Rhosin on Animal Tissues

The procedure of histological examination used in this example is as follows. The tissues were fixed in 4% paraformaldehyde overnight and then embedded in paraffin for histological examination. The transverse sections (4 μm) were incubated at 75~85° C. for 10 minutes, followed by stained with hematoxylin/eosin (HE), and examined under a light microscope. Severity of lesions was graded according to the methods described by Shackelford et al. (2002). Degree of lesions stained with HE was graded from one to five depending on severity: 1=minimal (<1%); 2=slight (1-25%); 3=moderate (26-50%); 4=moderate/severe (51-75%); 5=severe/high (76-100%). The result is shown in FIG. 11.

Figure 11:
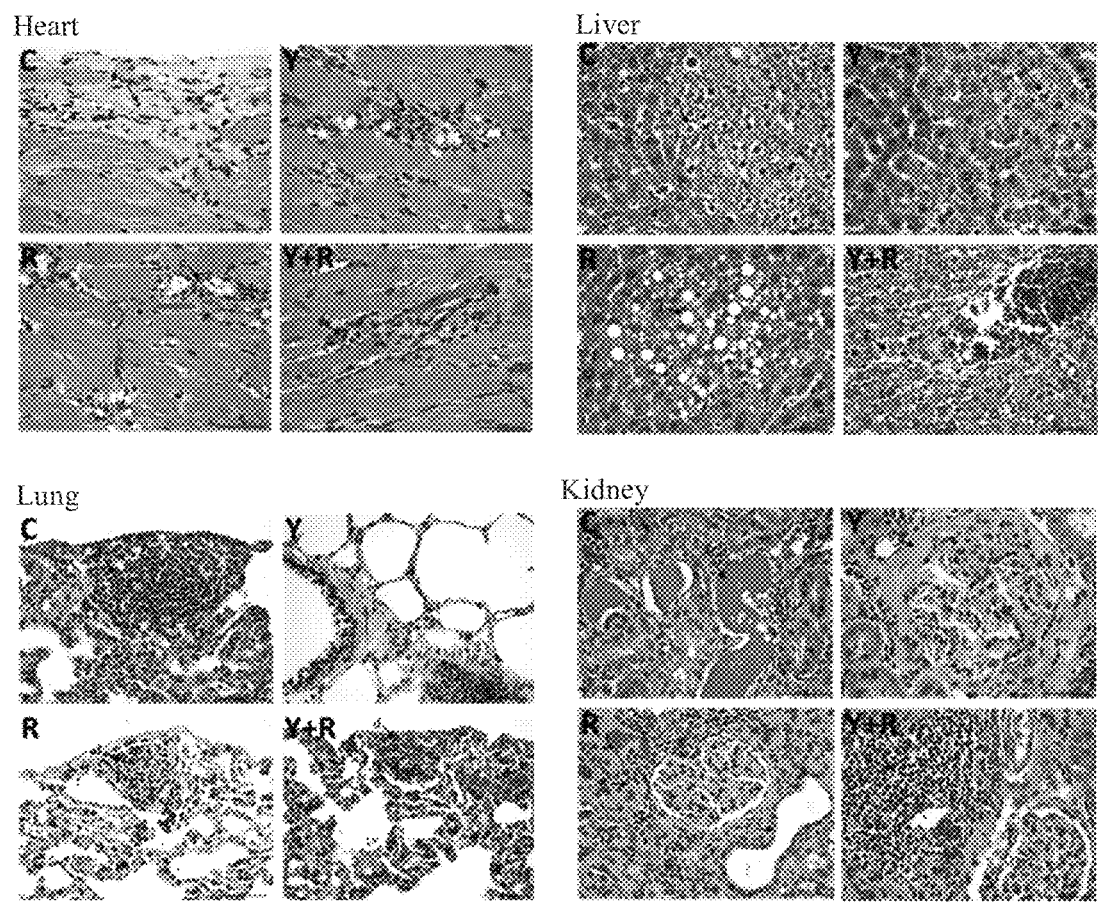
FIG. 11 shows the histological changes of Y16 and/or Rhosin on animal tissues, in which heart: C=control, grade=1, the heart presented minimal cardiomyopathy (arrow); Y=Y16 (20 mg/kg), grade=2, the heart presented slight cardiomyopathy (arrow); R=Rhosin (20 mg/kg), grade=2, the heart presented slight cardiomyopathy (arrow); Y+R=Y16 (5 mg/kg)+Rhosin (10 mg/kg), grade 2, the heart presented slight cardiomyopathy (arrow); liver: C=control, grade=1, the liver revealed minimal clear cell foci (arrow); Y=Y16 (20 mg/kg), grade=1, the liver revealed minimal clear cell foci (arrow); R=Rhosin (20 mg/kg), grade=1, the liver revealed minimal fatty change (arrow); Y+R=Y16 (5 mg/kg)+Rhosin (10 mg/kg), grade=1, the liver revealed minimal fatty change (arrow); lung: C=control, grade=1, the lung showed minimal subpleural infiltration of mononuclear cells (arrow); Y=Y16 (20 mg/kg), grade=1, no significant histopathological changes of lung were noted; R=Rhosin (20 mg/kg), grade=1, the lung showed minimal subpleural infiltration of mononuclear cells (arrow); Y+R=Y16 (5 mg/kg)+Rhosin (10 mg/kg), grade=1, the lung showed minimal subpleural infiltration of mononuclear cells (arrow); kidney: C=control, grade=2, the kidney demonstrated slight renal tubular cast (arrow), minimal renal tubular regeneration (arrow); Y=Y16 (20 mg/kg), grade=1, the kidney demonstrated minimal fibrosis (arrow) of interstitium and glomerulus; R=Rhosin (20 mg/kg), grade=1, the kidney demonstrated minimal renal tubular regeneration (arrow) and minimal fibrosis (arrow) of interstitium and glomerulus; Y+R=Y16 (5 mg/kg)+Rhosin (10 mg/kg), grade=1, the kidney demonstrated minimal infiltration of mononuclear cells (arrow).

FIG. 11 shows the histological changes of Y16 and/or Rhosin on animal tissues, in which heart: C=control, grade=1, the heart presented minimal cardiomyopathy (arrow); Y=Y16 (20 mg/kg), grade=2, the heart presented slight cardiomyopathy (arrow); R=Rhosin (20 mg/kg), grade=2, the heart presented slight cardiomyopathy (arrow); Y+R=Y16 (5 mg/kg)+Rhosin (10 mg/kg), grade 2, the heart presented slight cardiomyopathy (arrow); liver: C=control, grade=1, the liver revealed minimal clear cell foci (arrow); Y=Y16 (20 mg/kg), grade=1, the liver revealed minimal clear cell foci (arrow); R=Rhosin (20 mg/kg), grade=1, the liver revealed minimal fatty change (arrow); Y+R=Y16 (5 mg/kg)+Rhosin (10 mg/kg), grade=1, the liver revealed minimal fatty change (arrow); lung: C=control, grade=1, the lung showed minimal subpleural infiltration of mononuclear cells (arrow); Y=Y16 (20 mg/kg), grade=1, no significant histopathological changes of lung were noted; R=Rhosin (20 mg/kg), grade=1, the lung showed minimal subpleural infiltration of mononuclear cells (arrow); Y+R=Y16 (5 mg/kg)+Rhosin (10 mg/kg), grade=1, the lung showed minimal subpleural infiltration of mononuclear cells (arrow); kidney: C=control, grade=2, the kidney demonstrated slight renal tubular cast (arrow), minimal renal tubular regeneration (arrow); Y=Y16 (20 mg/kg), grade=1, the kidney demonstrated minimal fibrosis (arrow) of interstitium and glomerulus; R=Rhosin (20 mg/kg), grade=1, the kidney demonstrated minimal renal tubular regeneration (arrow) and minimal fibrosis (arrow) of interstitium and glomerulus; Y+R=Y16 (5 mg/kg)+Rhosin (10 mg/kg), grade=1, the kidney demonstrated minimal infiltration of mononuclear cells (arrow).

According to the histological analyses of the rats' heart, liver, lungs, and kidneys, the Y16 and Rhosin doses used in the experiments did not cause any overt injuries to the rats. There were no significant differences between the experimental groups and the control groups. These indicated that the mild damage in these tissues might not be caused by the drugs Y16 or Rhosin, but might be due to surgical procedure used in the experiments (FIG. 11).

In summary, the compound (Y16 and/or Rhosin) of the present invention inhibits interaction between LARG and a RhoA protein in VSMCs by in vitro cell experiments, reduces phosphorylation of MYPT1 in VSMCs, and effectively reduces the blood pressure of spontaneously hypertensive rats by in vivo animal experiments, thereby achieving the effect of treating hypertension. Therefore, the small molecule compounds of Y16, Rhosin or a combination thereof are used in the present invention, and developed as a therapeutic drug for lowering blood pressure. It is effective whether it is administered orally or injected. By injection, blood pressure can be lowered quickly, and within different doses, blood pressure can be lowered by 20-40% within one hour. Compared with traditional antihypertensive drugs (i.e., angiotensin II receptors), its superiority is even greater. If it is made into an oral dosage form, it can be adjusted to an appropriate antihypertensive effect according to different doses and dynamic changes of the drug. Y16 and Rhosin achieve the effect of lowering blood pressure by inhibiting Rho guanine nucleotide exchange factor (Rho GEF)/LARG small G protein, the downstream of the signaling transduction pathway of angiotensin II receptor, thereby blocking the activation of Rho A/Rho kinase and MLCP. Its role is specific. The compound of the present invention are different from angiotensin type II receptors, which block all the signal transductions after the receptors, including positive (lowering blood pressure) and negative (side effect) effects without specificity. In addition, from the observation of animal experiments, high-dose Y16 or Rhosin does not cause changes in animal blood (blood cells), organs (e.g., heart, lung, liver, and kidney) and tissues.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A method for treating hypertension, comprising:
administering to a subject in need thereof a pharmaceutical composition comprising an effective amount of a compound, wherein the compound is selected from the group consisting of: (E)-4-(3-(3-methyl benzyloxy)benzylidene)-1-phenylpyrazolidine-3,5-dione, (2R)-2-amino-3-(1H-indol-3-yl)-N-[(E)-quinoxalin-6-ylmethylideneamino]propenamide, and a combination thereof, wherein when the (E)-4-(3-(3-methyl benzyloxy)benzylidene)-1-phenylpyrazolidine-3,5-dione is administered alone, the effective amount of the (E)-4-(3-(3-methyl benzyloxy)benzylidene)-1-phenylpyrazolidine-3,5-dione is at least 5 mg/kg.

2. The method according to claim 1, wherein the hypertension is spontaneous hypertension.

3. The method according to claim 2, wherein the spontaneous hypertension is treated by inhibiting interaction between leukemia-associated Rho guanine nucleotide exchange factor (LARG) and a RhoA protein in a vascular smooth muscle cell (VSMC).

4. The method according to claim 2, wherein the spontaneous hypertension is treated by reducing phosphorylation of myosin phosphatase target subunit 1 (MYPT1) in a vascular smooth muscle cell (VSMC).

5. The method according to claim 1, wherein when the (2R)-2-amino-3-(2,3-dihydro-1H-inden-1-yl)-N'-((E)-quinolin-7-ylmethylene)propane hydrazide is administered alone, the effective amount of the (2R)-2-amino-3-(1H-indol-3-yl)-N-[(E)-quinoxalin-6-ylmethylideneamino]propenamide is at least 10 mg/kg.

6. The method according to claim 1, wherein when the (E)-4-(3-(3-methyl benzyloxy)benzylidene)-1-phenylpyrazolidine-3,5-dione and the (2R)-2-amino-3-(1H-indol-3-yl)-N-[(E)-quinoxalin-6-ylmethylideneamino]propenamide are administered in combination, the effective amount of the (E)-4-(3-(3-methyl benzyloxy)benzylidene)-1-phenylpyrazolidine-3,5-dione is at least 3 mg/kg, and the effective amount of the (2R)-2-amino-3-(2,3-dihydro-1H-inden-1-yl)-N'-((E)-quinolin-7-ylmethylene)propane hydrazide is at least 7 mg/kg.

7. The method according to claim 1, wherein the pharmaceutical composition further comprises a pharmaceutically acceptable carrier.

8. The method according to claim 1, wherein the pharmaceutical composition is in a dosage form for parenteral administration.

9. The method according to claim 1, wherein the pharmaceutical composition is in a dosage form for oral administration.

* * * * *